(12) United States Patent
Akiyama et al.

(10) Patent No.: US 9,459,182 B2
(45) Date of Patent: Oct. 4, 2016

(54) MICROCHIP AND PARTICLE ANALYZING APPARATUS

(75) Inventors: Yuji Akiyama, Tokyo (JP); Shoji Akiyama, Tokyo (JP); Takeshi Yamasaki, Tokyo (JP)

(73) Assignee: Sony Corporation, Tokyo (JP)

( * ) Notice: Subject to any disclaimer, the term of this patent is extended or adjusted under 35 U.S.C. 154(b) by 227 days.

(21) Appl. No.: 14/234,469

(22) PCT Filed: Jun. 29, 2012

(86) PCT No.: PCT/JP2012/004215
§ 371 (c)(1),
(2), (4) Date: Jan. 23, 2014

(87) PCT Pub. No.: WO2013/018273
PCT Pub. Date: Feb. 7, 2013

(65) Prior Publication Data
US 2014/0174206 A1    Jun. 26, 2014

(30) Foreign Application Priority Data
Aug. 3, 2011  (JP) ................................ 2011-169726

(51) Int. Cl.
*G01N 1/00* (2006.01)
*B01L 3/02* (2006.01)
(Continued)

(52) U.S. Cl.
CPC ............... *G01N 1/00* (2013.01); *B01L 3/0268* (2013.01); *B01L 3/502776* (2013.01);
(Continued)

(58) Field of Classification Search
CPC ........... B01L 3/0268; B01L 3/502761; B01L 3/502776; B01L 2200/0636; B01L 2300/0877; B01L 2300/089; B01L 9/527; G01N 15/1404; G01N 15/1484; G01N 15/1056; G01N 1/00; G01N 21/01
USPC .......................................................... 73/863
See application file for complete search history.

(56) References Cited

U.S. PATENT DOCUMENTS 7,391,020 B2 *  6/2008  Bousse ................... B05B 5/025
                                                        250/281
7,651,665 B2 *  1/2010  Gonzalez .............. B01L 3/0268
                                                        422/400
(Continued)

FOREIGN PATENT DOCUMENTS

CN      101609088      12/2009
EP       2135675       12/2009
(Continued)

OTHER PUBLICATIONS

Office Action issued in connection with Japanese Patent Application No. 2011-169726, dated Jun. 30, 2015. (3 pages).
(Continued)

*Primary Examiner* — Freddie Kirkland, III
(74) *Attorney, Agent, or Firm* — K&L Gates LLP

(57) ABSTRACT

There is provided a microchip including a flow channel, an ejection portion, and a cutout portion. The flow channel is configured to convey a fluid therein. The ejection portion includes an opening directed toward an end face of a substrate layer, and the ejection portion is configured to eject the fluid flowing through the flow channel to outside. The substrate layer is laminated to each other. The cutout portion is formed between the opening of the ejection portion and the end face of the substrate layer. The cutout portion has a larger diameter than that of the opening.

14 Claims, 10 Drawing Sheets

(51) Int. Cl.
 *G01N 21/01* (2006.01)
 *B01L 3/00* (2006.01)
 *G01N 15/14* (2006.01)

(52) U.S. Cl.
 CPC ......... *G01N 15/1484* (2013.01); *G01N 21/01* (2013.01); *B01L 3/502707* (2013.01); *B01L 2200/0652* (2013.01); *B01L 2200/12* (2013.01); *B01L 2300/0816* (2013.01); *B01L 2300/0887* (2013.01); *B01L 2400/0433* (2013.01); *B01L 2400/0487* (2013.01); *G01N 2015/149* (2013.01)

(56) References Cited

U.S. PATENT DOCUMENTS

| | | | |
|---|---|---|---|
| 8,096,421 B2* | 1/2012 | Shinoda | B01L 3/502761 209/44.2 |
| 8,246,805 B2* | 8/2012 | Shinoda | B01F 3/0819 204/451 |
| 8,657,121 B2* | 2/2014 | Shinoda | B01L 3/0268 209/552 |
| D704,580 S * | 5/2014 | Akiyama | D10/81 |
| 9,176,042 B2* | 11/2015 | Ito | B01L 3/502776 |

| | | | |
|---|---|---|---|
| 2006/0022130 A1 | 2/2006 | Bousse et al. | |
| 2006/0051250 A1 | 3/2006 | Gonzalez et al. | |
| 2009/0308473 A1 | 12/2009 | Shinoda | |

FOREIGN PATENT DOCUMENTS

| | | |
|---|---|---|
| GB | 2370519 | 7/2002 |
| JP | 03-164256 | 7/1991 |
| JP | H0985156 | 3/1997 |
| JP | 2003334760 | 11/2003 |
| JP | 2004-069499 | 3/2004 |
| JP | 2006-192622 | 7/2006 |
| JP | 2010-025911 | 2/2010 |
| JP | 2010-190680 | 9/2010 |

OTHER PUBLICATIONS

The State Intellectual Property Office of the People'S Republic of China, Notification of the First Office Action issued in connection with PRC Patent Application No. 2012800376112, dated Oct. 8, 2014. (14 pages).

Office Action issued in connection with Japanese Patent Application No. 2011-169726, dated Jan. 19, 2016. (4 pages).

* cited by examiner (A)

(B)

(A)

(B)

(C)

MICROCHIP AND PARTICLE ANALYZING APPARATUS

CROSS REFERENCES TO RELATED APPLICATIONS

The present application is a national stage of International Application No. PCT/JP2012/004215 filed on Jun. 29, 2012 and claims priority to Japanese Patent Application No. 2011-169726 filed on Aug. 3, 2011, the disclosure of which is incorporated herein by reference.

BACKGROUND

The present disclosure relates to microchips. More particularly, embodiments of the present disclosure relate to a microchip used in analyzing particles such as cells or the like.

Recently developed microchips are provided with regions or channels which are formed to perform a chemical or biological analysis on a substrate made of silicon, glass, or the like by employing micromachining techniques used in the semiconductor industry. Analysis systems using such microchips are called a micro-total-analysis system (micro-TAS), lab-on-a-chip, biochip or the like. These analysis systems are paid attention to as technology capable of enhancing the speed, efficiency, or integration of analysis, and further capable of providing a compact analyzing apparatus.

The micro-TAS is used in a case where an analysis is performed with small amount of samples or a case where microchips are designed for disposable use, thus the micro-TAS is particularly expected to be applied to a biological analysis which deals with valuable and very small amount of samples or a large number of specimens. As an application example of the micro-TAS, electrochemical detectors and compact-sized electrochemical sensors are presented. The electrochemical detectors are used in liquid chromatography, and the compact-sized electrochemical sensors are used in clinical or medical practice.

As another application example of the micro-TAS, there is a technology in which particles such as cells, micro-beads, and so on are analyzed in a channel provided on a microchip. In this technology, the characteristics of particles are analyzed in an optical, electrical or magnetic manner. In this particle analyzing technology, when there is a population (group) which is determined that a predetermined condition is satisfied according to the analyzed results, the population is separated and collected from among particles.

Patent Literature 1, for example, discloses "a microchip including a flow path through which liquid containing micro particle flows, an orifice through which the liquid flowing through the flow path is discharged to a space outside the chip, and a light-irradiated portion disposed in a predetermined location of the flow path for detecting an optical property of the micro particle". The microchip disclosed in Patent Literature 1 is used to sort the micro particle determined to have a predetermined optical property by controlling movement directions of a liquid drop containing the micro particle discharged from the orifice.

CITATION LIST

Patent Literature

[PTL 1]
Japanese Patent Application Laid-open No. 2010-190680

SUMMARY

Technical Problem

In the particle analyzing microchip such as described in Patent Literature 1, in order to accurately control a flow direction of droplets ejected from an orifice and to properly separate and sort the particles, it will be necessary to stably eject the droplets of regular size and shape from the orifice and to maintain a steady ejecting path.

In light of the foregoing, it is desirable to provide a microchip capable of steady ejecting droplets of regular size and shape from an orifice and maintaining a steady ejecting path in a cost-effective and easy manner without using expensive materials or undergoing complicated molding processes.

Solution to Problem

According to an embodiment of the present disclosure, there is provided a microchip including a flow channel, an ejection portion, and a cutout portion. The flow channel is configured to convey a fluid therein. The ejection portion includes an opening directed toward an end face of a substrate layer, and the ejection portion is configured to eject the fluid flowing through the flow channel to outside. The substrate layer is laminated to each other. The cutout portion is formed between the opening of the ejection portion and the end face of the substrate layer. The cutout portion has a larger diameter than that of the opening. The microchip according to the embodiment may further include a connection portion, configured to have a straight line shape, for connecting the flow channel to the ejection portion.

In the microchip according to the embodiment, the cutout portion is provided between the opening of the ejection portion and the end face of the substrate layer, and the ejection portion is provided at a position recessed inwardly by a predetermined distance from the end face of the substrate layer susceptible to molding defect due to injection molding. The opening of the ejection portion therefore can be prevented from being irregular in shape, thereby forming the ejection portion having a desired shape.

In the microchip of the embodiment, the ejection portion is provided at a position recessed inwardly by a predetermined distance from the end face of the substrate layer susceptible to deformation due to thermocompression bonding. The shape of the ejection portion and the shape of the connection portion arranged to connect the flow channel with the ejection portion thus can be prevented from being deformed. Also, the ejection portion and flow channel having desired shapes can be formed.

In the microchip of the embodiment, the cutout portion preferably has a width of 0.2 millimeters or more in corresponding with a distance between the opening and the end face.

The cutout portion having a width of 0.2 millimeters or more allows molding defect caused due to injection molding or deformation caused due to thermocompression bonding to be prevented certainly.

The microchip according to the embodiment of the present disclosure is preferably used in analyzing particles. There is also provided a particle analyzing apparatus having the microchip mounted thereon.

As used herein, the term "particle(s)" should be broadly construed to include bioparticles such as cell, microorganism, and liposome as well as synthetic particles such as latex particles, gel particles, and industrial particles. Examples of the bioparticles include chromosome, liposome, mitochondria, and organelle (cell compartment) constituting various cells. Examples of the cells include animal cells (e.g., blood corpuscle cells) and plant cells. Examples of the microorganisms include bacteria such as colon bacillus, viruses such as tobacco mosaic virus, and fungi such as yeast. Examples of the microscopic bioparticles include microscopic biopolymers such as nucleic acid, proteins, and complexes thereof. The industrial particles may be, for example, organic or inorganic polymer materials, metals or the like. The organic polymer materials include polystyrene, stylenevinyl benzene, and polymethyl methacrylate. Examples of the inorganic polymer materials include glass, silica, and magnetic materials. Examples of the metals include gold colloid and alumina. The shapes of these particles are typically spherical, but may be non-spherical. In addition, embodiments of the present disclosure are not particularly limited to factors such as particle size or mass.

Advantageous Effects of Invention

According to the embodiments of the present disclosure, there is provided a microchip capable of stably ejecting droplets of regular size and shape from an orifice and maintaining a steady ejecting path in a cost-effective and easy manner without using expensive materials or undergoing complicated molding processes.

Additional features and advantages are described herein, and will be apparent from the following Detailed Description and the figures.

DETAILED DESCRIPTION

Figure 1:
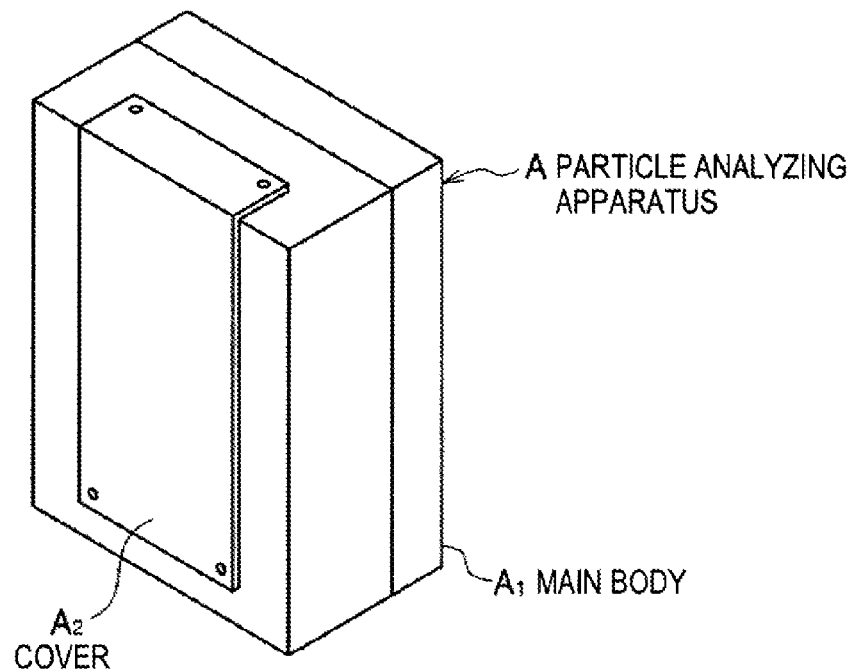
FIGS. 1A and 1B is chematic diagrams illustrating a configuration of a particle analyzing apparatus A according to an embodiment of the present disclosure.
Figure 1:
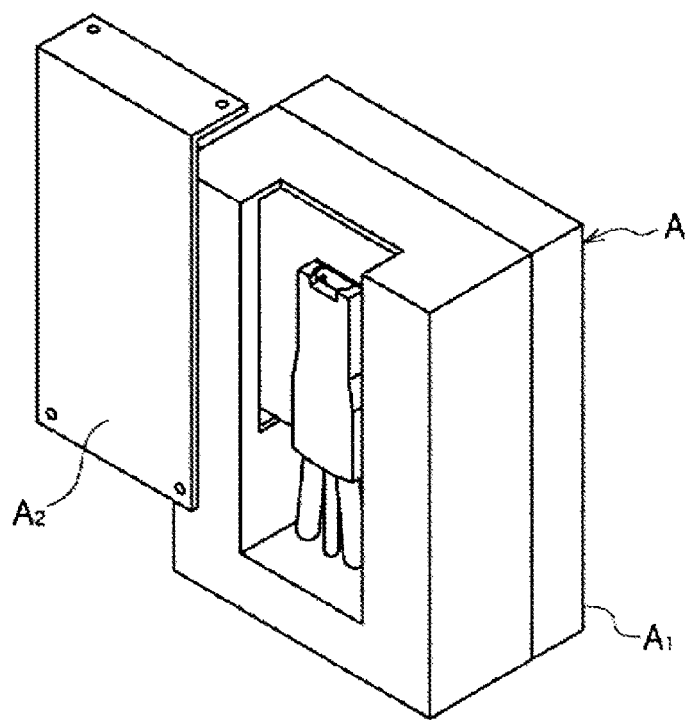

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Figure 2:
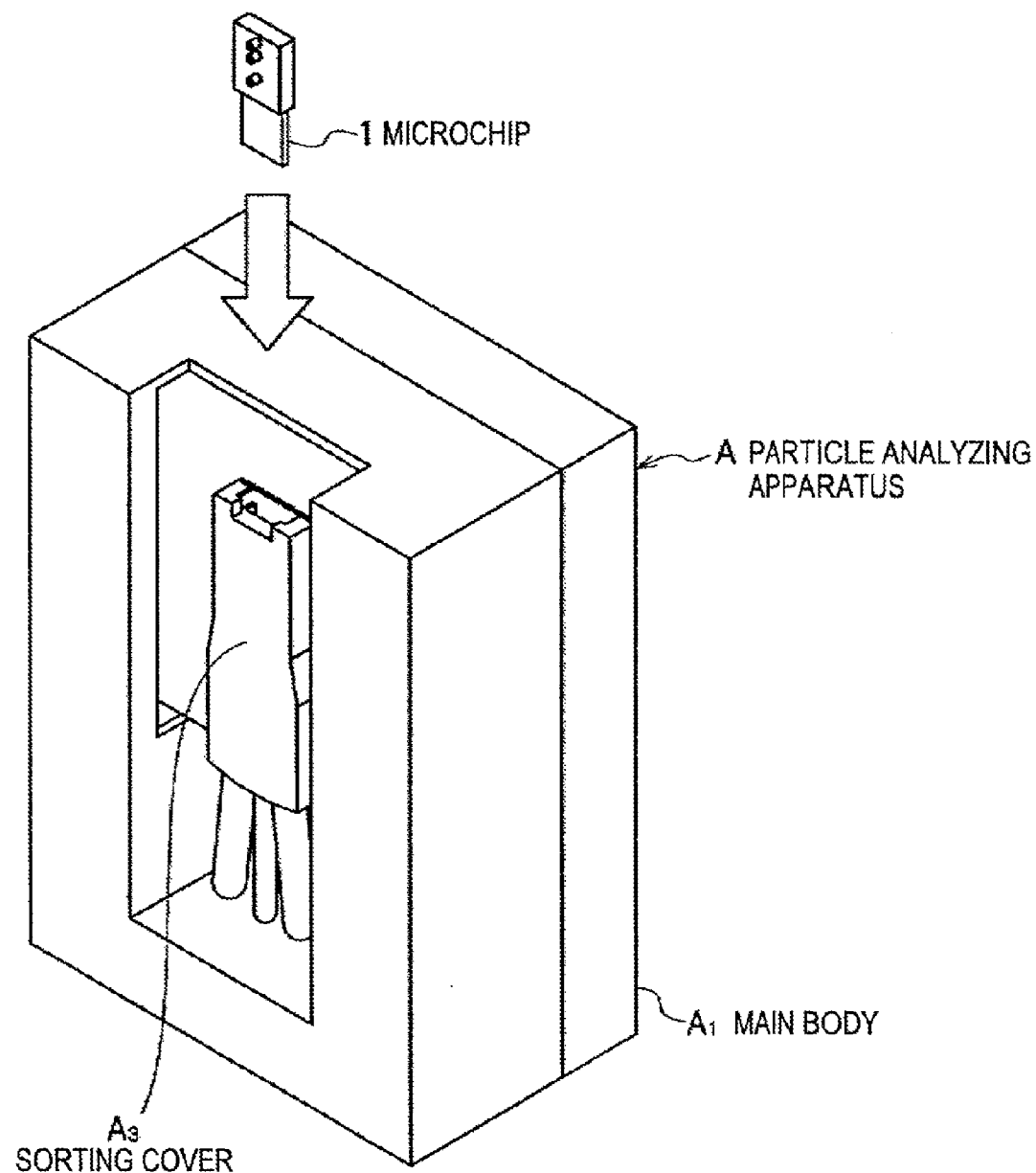
FIG. 2 is a schematic diagram illustrating a configuration of the particle analyzing apparatus A according to an embodiment of the present disclosure.
Figure 3:
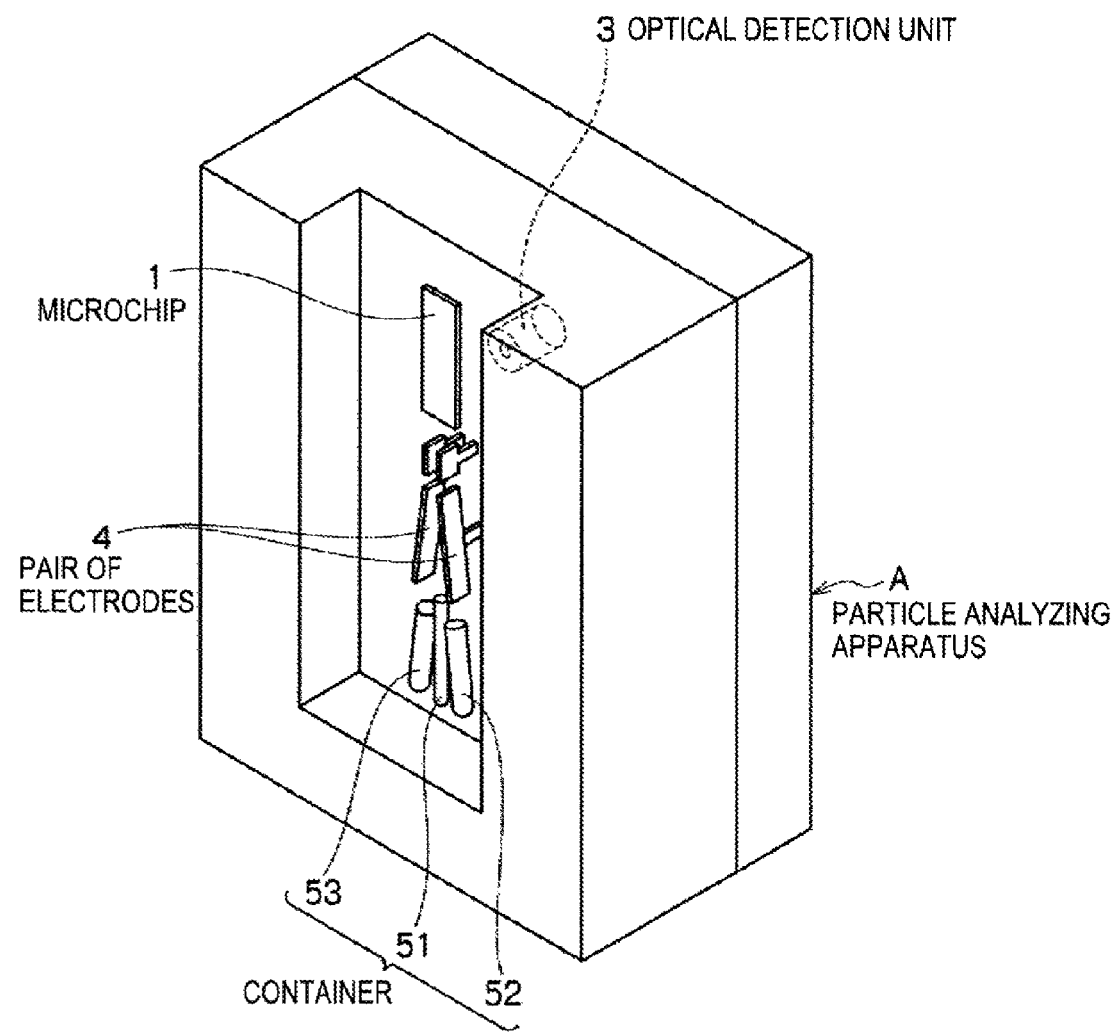
FIG. 3 is a schematic diagram illustrating a configuration of the particle analyzing apparatus A according to an embodiment of the present disclosure.

The description will be given in the following order.
1. Particle Analyzing Apparatus
2. Microchip
3. Operation of Particle Analyzing apparatus
1. Particle Analyzing Apparatus FIGS. 1 to 4 are schematic diagrams illustrating configurations of a particle analyzing apparatus according to an embodiment of the present disclosure. In these figures, the particle analyzing apparatus A includes a particle sorting region protected by a cover $A_2$ of a main body $A_1$. This particle sorting region is further protected by a sorting cover $A_3$. The particle sorting region is configured to include a microchip 1 which is inserted and mounted into a top opening of the sorting cover $A_3$. In FIG. 2, a block-shaped arrow indicates an insertion direction along which a microchip module is inserted into the sorting cover $A_3$. The microchip module includes the microchip 1 as a constituent element thereof. The illustration of the sorting cover $A_3$ is omitted in FIG. 3 for the convenience of explanation. Further, only the microchip 1 of the microchip module inserted into the sorting cover $A_3$ is shown in FIG. 3, and other portions of the microchip module are omitted.

The particle sorting region includes the microchip 1, an optical detection unit 3, a pair of electrodes 4, 4 and three collection units (containers 51, 52, and 53). The optical detection unit 3 irradiates a light onto a predetermined area of the microchip 1. The optical detection unit 3 and the pair of electrodes 4, 4 are provided in the main body $A_1$. Each of the containers 51, 52 and 53 is detachably mounted to the main body $A_1$.

Figure 4:
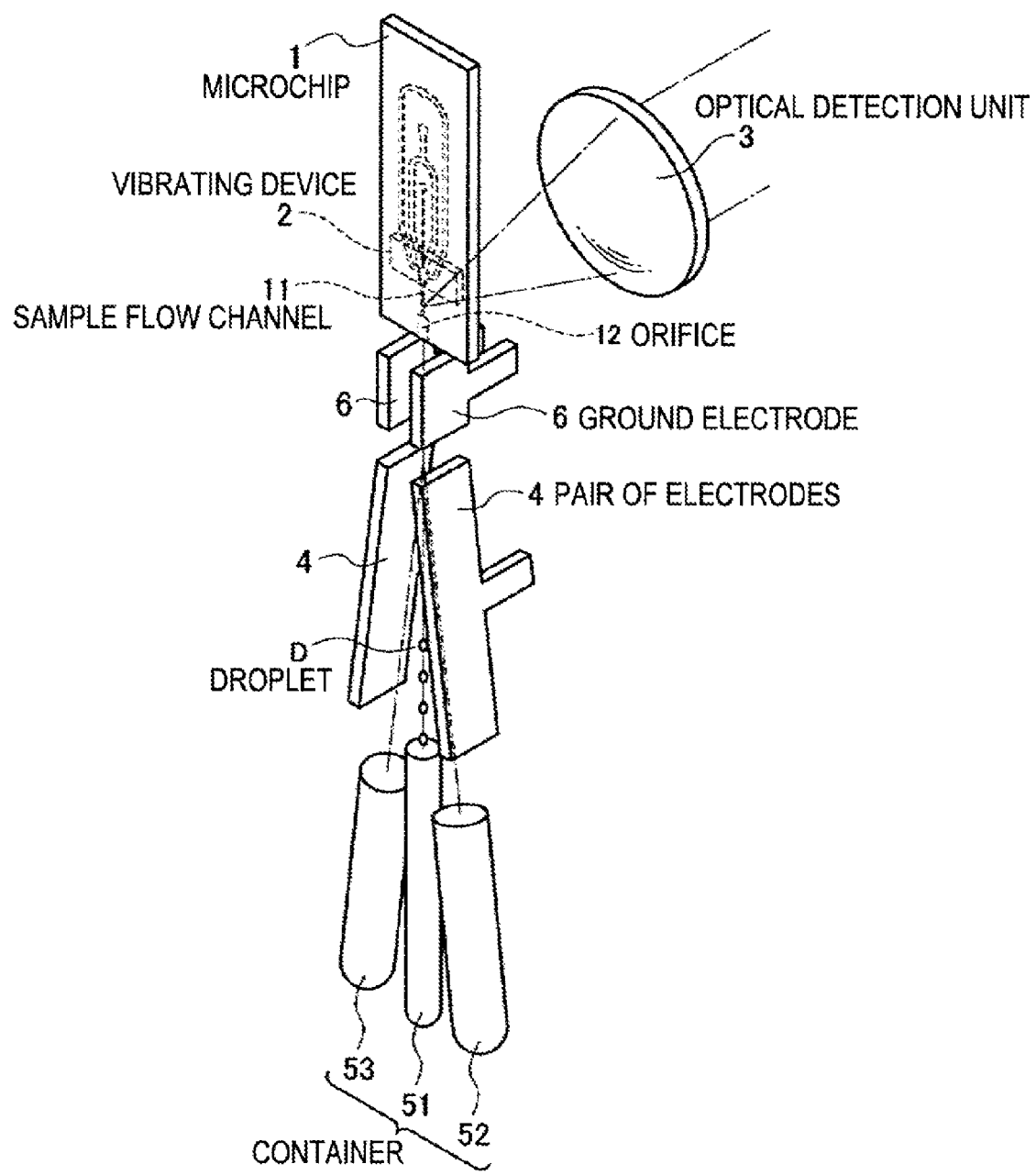
FIG. 4 is a schematic diagram illustrating a configuration of the particle analyzing apparatus A according to an embodiment of the present disclosure.

A configuration of the particle sorting region will be described in detail below with reference to FIG. 4. FIG. 4 illustrates the microchip 1, the optical detection unit 3, the pair of electrodes 4, 4, the container 51 to 53, and so on. As shown in FIG. 4, a vibrating device 2 is provided on the microchip 1. Electrodes 6, 6 are connected to the ground.

The microchip 1 includes a sample flow channel 11. A stream of fluid containing the particle to be sorted flows through the sample flow channel 11 (the fluid is referred to hereinafter as a "sample fluid"). The optical detection unit 3 irradiates a light onto a predetermined area of the sample flow channel 11 (the light is referred to hereinafter as a "measuring light"). The optical detection unit 3 also detects a light emitted from the particles flowing through the sample flow channel 11 (the light is referred to hereinafter as a "light to be measured"). The area which is irradiated with the measuring light by the optical detection unit 3 in the sample flow channel 11 is hereinafter referred to as a "light irradiation area".

The optical detection unit 3 may be structurally similar to that used in a particle analyzing apparatus in the related art. More specifically, the optical detection unit 3 includes a laser light source, an irradiation system, and a detection system. The irradiation system includes a condensing lens or diachronic mirror configured to condense and irradiate a laser light onto particles, and a band pass filter. The detection system is arranged to detect the light to be measured which is emitted from the particles in response to the irradiation of the laser light. The detection system is configured to include a photo multiplier tube (PMT), or an area image-capturing device such as a charge coupled device (CCD) or complementary metal-oxide semiconductor (CMOS) device. In the FIG. 4, only the condensing lens is illustrated as the optical detection unit 3. In FIG. 4, the irradiation and detection systems are arranged so that they have a common flow channel, but the irradiation and detection systems may be arranged to have the respective flow channels.

The light to be measured is detected by the detection system of the optical detection unit 3 and is emitted from the particles in response to the irradiation of the laser light. Examples of the light to be measured may include a forward scatter, a side scatter, a scattered light such as Rayleigh scattering or Mie scattering, or fluorescence. The light to be measured is converted into electrical signals. The optical characteristics of the particles are detected on the basis of the electrical signal.

The sample fluid is passed through the light irradiation area and then is ejected from an orifice 12 to the outside of the microchip. The orifice 12 (also referred to as an ejection portion) is provided at one end of the sample flow channel 11. In this case, The microchip 1 is vibrated by the vibrating device 2 such as a piezo-electric element and thus the sample fluid can be broken into individual droplets and be ejected to the outside of the microchip. That is, the droplet D is ejected to the outside of the microchip.

The droplet D may contain respective particles to be sorted. The pair of electrodes 4, 4 are arranged along the flow direction of droplets ejected to the outside of the microchip. The pair of electrodes 4, 4 are arranged to be faced each other so that the droplets may be passed between the electrodes. An electric charge applying device (not shown) applies electric charge to the ejected droplet. The flow directions of droplets are controlled by an electrostatic repulsive force (or an electrostatic attractive force) acting between the pair of electrode 4, 4 and the droplet which is charged with any electric charge. The pair of electrode 4, 4 allows the droplets to be diverted and guided into respective corresponding one of the containers 51, 52, and 53.

The flow directions of droplets containing individual particles are controlled by the pair of electrode 4, 4 based on the optical characteristics of individual particles detected by the optical detection unit 3. Thus, the particle analyzing apparatus A can collect and sort the particles with desired characteristics into respective corresponding one of the containers 51 to 53.

In the particle analyzing apparatus A, electric or magnetic detection device may be used instead of the optical detection unit 3. When the characteristics of particles are intended to be detected in an electrical or magnetic manner, microelectrodes are arranged to be faced each other and the sample flow channel 11 is placed between the microelectrodes, thereby measuring resistance, capacitance, inductances, impedance, variations in electric field between the electrodes, magnetization, variations in magnetic field, variations in magnetic field, and so on. In this case, the particles are sorted on the basis of electrical or magnetic characteristics of the particles.

2. Microchip

Figure 5:
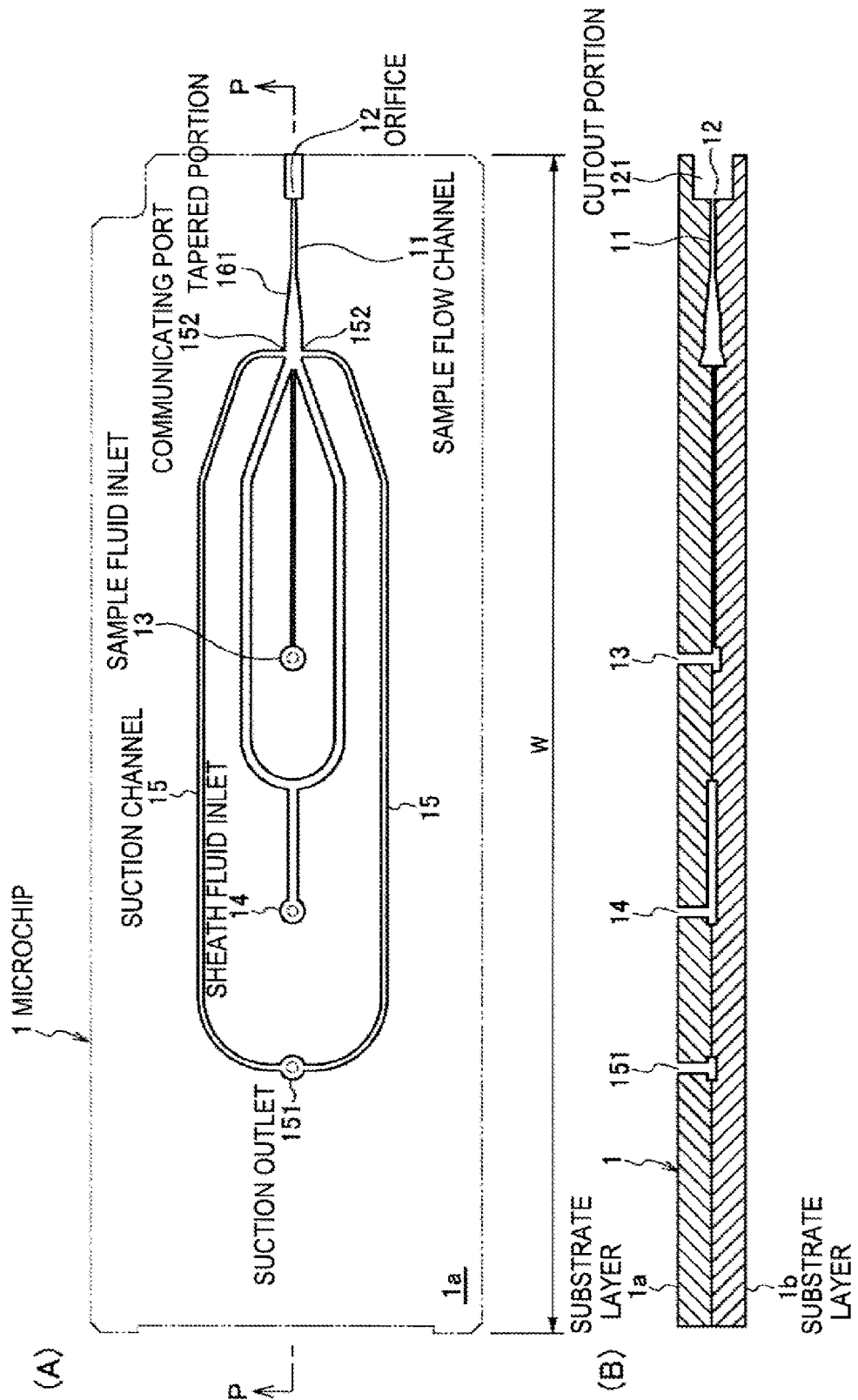
FIGS. 5A and 5B is schematic diagrams illustrating a configuration of a microchip 1 according to an embodiment of the present disclosure.
Figure 6:
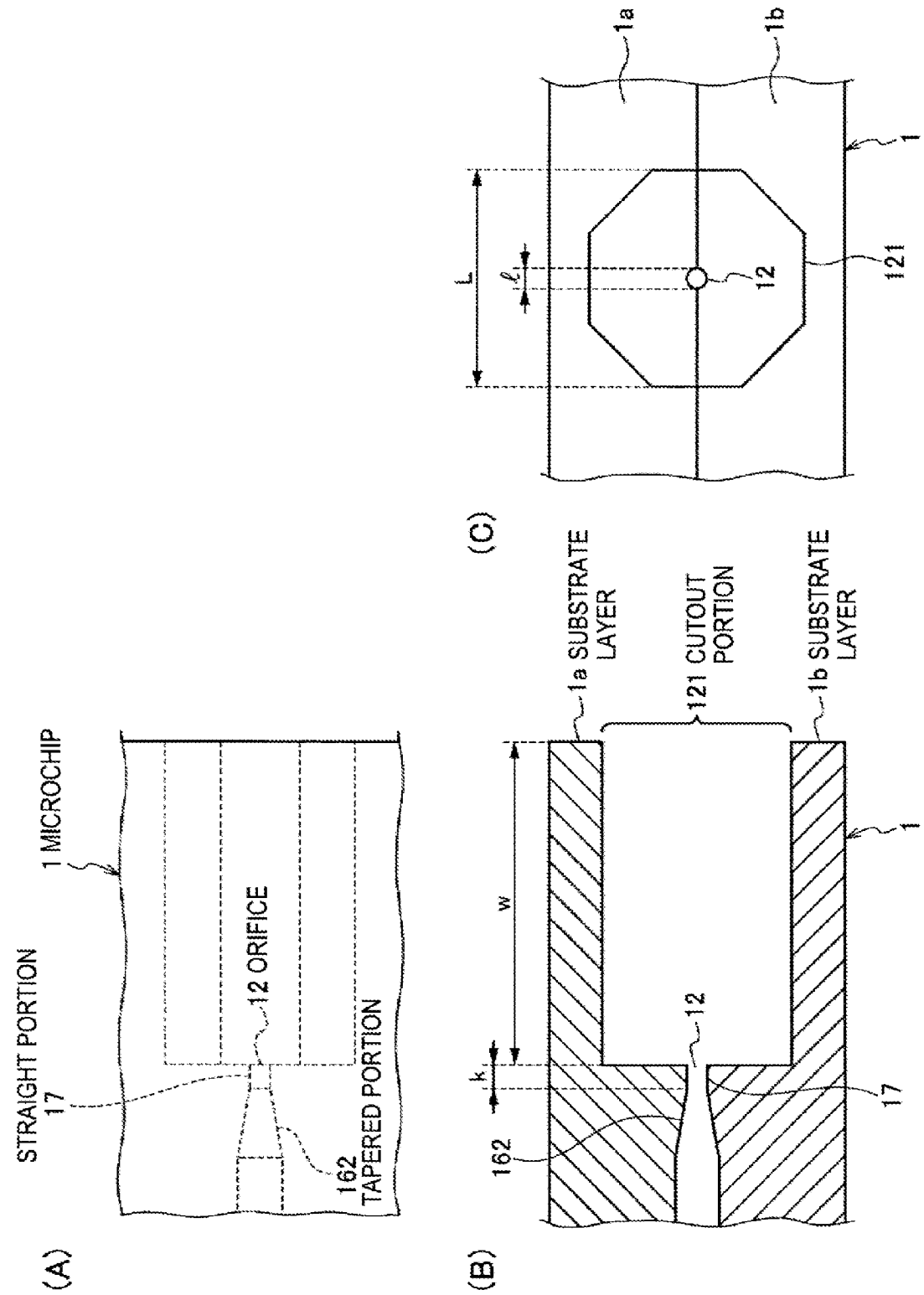
FIGS. 6A through 6C is schematic diagrams illustrating a configuration of an orifice 12 according to an embodiment of the present disclosure.

FIGS. 5A and 5B are schematic diagrams illustrating a configuration of the microchip 1. FIG. 5A shows a schematic top view and FIG. 5B shows a schematic sectional view taken along the line P-P of FIG. 5A. FIGS. 6A, 6B and 6C are schematic diagrams illustrating a configuration of the orifice 12 of the microchip 1. FIG. 6A shows a schematic top view, FIG. 6B shows a schematic sectional view taken along the line P-P of FIG. 5A, and FIG. 6C shows a front view.

In the microchip 1, substrate layers 1a, 1b are bonded to each other so as to form the sample flow channel 11. The sample flow channel 11 can be formed by injection molding of a thermoplastic resin using a mold. The sample flow channel 11 may be formed at either one or both of the substrate layers 1a, 1b. In the case where the sample flow channel 11 is formed at both of the substrate layers 1a, 1b, respective parts of the sample flow channel are partially formed on both layers.

As a material used in forming a typical microchip, the thermoplastic resin can employ a known plastic material such as polycarbonate, polymethyl methacrylate (PMMA), cyclic polyolefin, polyethylene, polystyrene, polypropylene, and polydimethyl siloxane (PDMS).

The injection molding may be implemented in the usual way. For example, when injection molding process is done by polyolefin (ZEONEX 1060R manufactured by Zeon Corporation) using the injection molding machine (SE75DU manufactured by Sumitomo Heavy Industries, Ltd.), the typical molding process is performed under conditions involving a resin temperature of 270 deg C., a mold temperature of 80 deg C., and a mold clamping force of 500 kilo-Newton (kN).

The substrate layers 1a, 1b forming the sample flow channel 11 are bonded to each other by thermocompression bonding using well known processes. For example, when the substrate layers made of polyolefin are bonded together by thermocompression bonding using the nano-imprint machine (Eitre6/8 manufactured by Canon Inc.), the typical compression bonding process is performed by pressing the substrate layers for several minutes under conditions involving a bonding temperature of 95 deg C. and a pressing force of 10 kilo-Newton.

The sample fluid flowing out from a sample fluid inlet 13 joins the sheath fluid flowing out from a sheath fluid inlet 14. The joined stream passes through the sample flow channel 11. More specifically, the sheath fluid flowing out from the sheath fluid inlet 14 branches into two directions and then joins the sample fluid flowing out from the sample fluid inlet 13 at a joining point, so that the sample fluid may be sandwiched between the two directional flows of the sheath fluid. Thus, the sample fluid is placed midway between the flows of the sheath fluid, thereby forming three-dimensional laminar flow.

When there are some clogging materials or bubbles within the sample flow channel 11, a suction channel 15 removes any clogging material or bubbles by causing the stream in the sample flow channel 11 to be temporarily flowed in the reverse direction. The reversing of the flow direction is implemented by a negative pressure applied to the sample flow channel 11. A suction outlet 151 is formed at one end of the suction channel 15. The suction outlet 151 is connected to a negative pressure source such as a vacuum pump. The other end of the suction channel 15 is communicated with the sample flow channel 11 through a communicating port 152.

Figure 7:
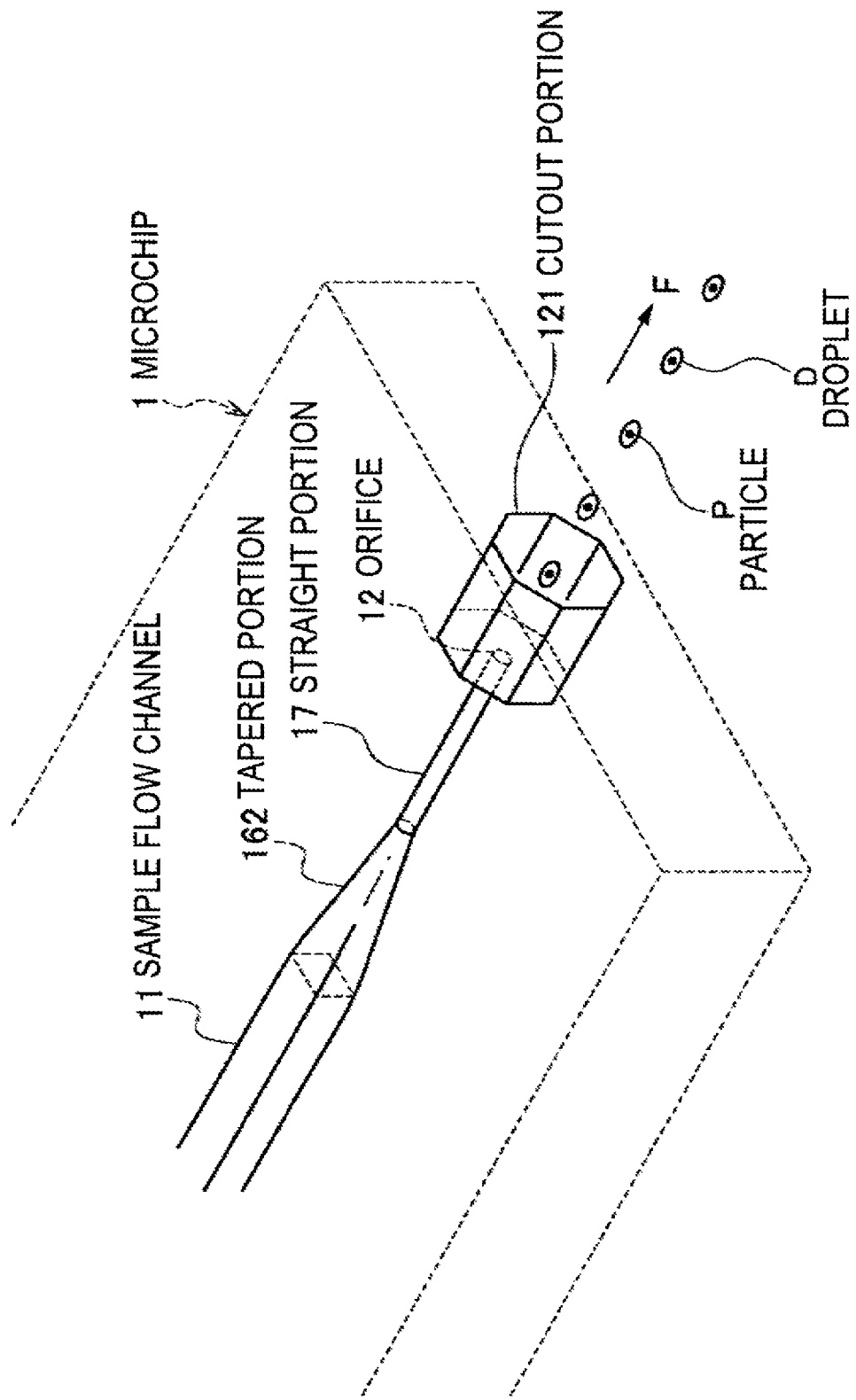
FIG. 7 is a schematic diagram illustrating a droplet D ejected from the orifice 12 according to an embodiment of the present disclosure.

The three-dimensional laminar flow is passed through a tapered portion 161 (see FIG. 5) or 162 (see FIG. 6) which is gradually thinned down along a fluid flowing direction, and then the three-dimensional laminar flow is ejected from the orifice 12 provided at one end of the sample flow channel. The tapered portion is formed such that the cross section profile of the tapered portion perpendicular to the fluid flowing direction is narrowed down in a gradual or stepwise manner according to the fluid flowing direction. As shown in FIG. 7, the droplet D is ejected from the orifice 12 to the outside of the microchip. In FIG. 7, the droplet D is ejected from the orifice 12 in an ejection direction F.

A straight portion 17 connects the sample flow channel 11 to the orifice 12 and is formed in a straight line shape. The straight portion 17 allows the droplet D to be ejected straight from the orifice 12 in the direction F indicated by an arrow. The straight portion 17 has a length (denoted as "k" in FIG. 6B) in a range from 100 micrometers to 500 micrometers when the orifice 12 has an opening diameter (denoted as "l" in FIG. 6C), for example, in a range from 30 micrometers to 250 micrometers. If the straight portion 17 has a length of 100 micrometers, then the ejection direction of the droplet D may be not constant. In this case, it will be difficult to precisely control the ejection direction of the droplet being ejected to the outside of the microchip.

The orifice 12 is opened toward the end face of the substrate layers 1a, 1b. A cutout portion 121 is provided between the opening of the orifice 12 and the end face of the substrate layers. The cutout portion 121 is formed by cutting out the substrate layers 1a, 1b between the opening of the orifice 12 and the end face of the substrate layers so that a diameter L of the cutout portion 121 may be larger than the opening diameter l of the orifice 12 (see FIG. 6C). The diameter L of the cutout portion 121 is preferably more than two times larger than the opening diameter l of the orifice 12 so that the flow of the droplets ejected from the orifice 12 may be prevented from being obstructed. However, if the diameter L of the cutout portion 121 is too large, then uniformity of a temperature or pressure distribution becomes worse, or gas is gathered in the cutout portion 121, and this becomes the cause of shape irregularity of the orifice 12. Therefore, the cutout portion 121 preferably has the diameter L in a range from 400 micrometers to about 2 millimeters, when the orifice 12 typically has the opening diameter l of about 200 micrometers.

In this embodiment, the opening of the orifice 12 has a circular shape and the cutout portion 121 is formed by cutting the substrate layers 1a, 1b in an octagonal prism shape. However, the opening of the orifice 12 is not limited to a circular shape, and may be oval, square, rectangular, or polygonal. The opening of the orifice 12 preferably has a symmetric shape so as to achieve symmetries of thermal conduction and pressure loading when the substrate layers 1a, 1b are bonded through thermocompression. The cutout portion 121 is not limited to an octagonal prism shape, and may be any shape as long as a space communicating with the opening of the orifice 12 is formed and the shape does not inhibit the flow of the droplet ejected from the orifice 12. The cutout portion 121 is preferably placed coaxial with the orifice 12, but the embodiment is not limited to this. If the thickness of the microchip 1 is thin, then the cutout portion 121 may be formed by cutting off all the end face of the substrate layers 1a, 1b in the thickness direction.

It is generally known that the molding defect called as "burr" or "undercut" are probably occurred at a portion which is contact with the mold of the thermoplastic resin when the substrate layer is fabricated by injection molding. In particular, the gas generated at the time of molding will cause any portions which will be the end face of the substrate layer and its surroundings to be significantly deformed. For this reason, if the opening of the orifice is formed at the end face of the substrate layer, then the molding defect makes it easier to cause the orifice to become more irregular in shape.

In the microchip 1 of the embodiment, the cutout portion 121 is provided between the opening of the orifice 12 and the end face of the substrate layer, and the orifice 12 is provided at a position recessed inwardly by a predetermined distance from the end face of the substrate layer. Therefore, even though molding defect is occurred at the end face of the substrate layer and its surroundings, such molding defect does not have an influence on the shape of the orifice 12. As a result, the opening of the orifice 12 can be accurately molded into a desired shape and the droplet D of regular size and shape can be ejected from the orifice 12.

In order to be completely free from the influence of molding defect occurred at the end face of the substrate layer and its surroundings, a width (denoted as "w" in FIG. 6B) of the cutout portion may be set to correspond to the distance from the opening of the orifice 12 to the end face of the substrate layer. As an example, when a width (denoted as "W" in FIG. 5) of the microchip 1 in the direction from the orifice 12 to the end face of the substrate layer is 75 millimeters (the microchip size: 75 millimeters, 25 millimeters and 2 millimeters in width, length, and thickness, respectively), the width of the cutout portion is preferably 0.2 millimeters or more. The "burr" or gas occurred when performing an injection molding process depends on the types or conditions of the thermoplastic resin, and thus the width w of the cutout portion 121 is preferably set to be changed over a wide range and to be optimized, depending on the types or conditions of the thermoplastic resin.

It has been known that the end face of the substrate layer and its surrounding edges are likely to be susceptible to deformation due to thermal contraction as compared to a middle portion of the substrate layer, when a thermocompression bonding process is performed on the substrate layer. Thus, when the opening of the orifice or a flow channel connected thereto is provided at the end face of the substrate layer and its vicinities, the shape of the molded orifice or flow channel is likely to be deformed due to the thermal contraction.

In the microchip 1 of the embodiment, the cutout portion 121 is provided between the opening of the orifice 12 and the end face of the substrate layer, and the orifice 12 is provided at a position recessed inwardly by a predetermined distance from the end face of the substrate layer. Therefore, when a thermocompression bonding process is performed on the substrate layer, the shape of the orifice or flow channel connected thereto will not be deformed. As a result, in the microchip 1, the shapes of the orifice 12 and straight portion 17 can be maintained in the desired shape and the droplet D of regular size and shape can be ejected straight from the orifice 12.

Figure 9:
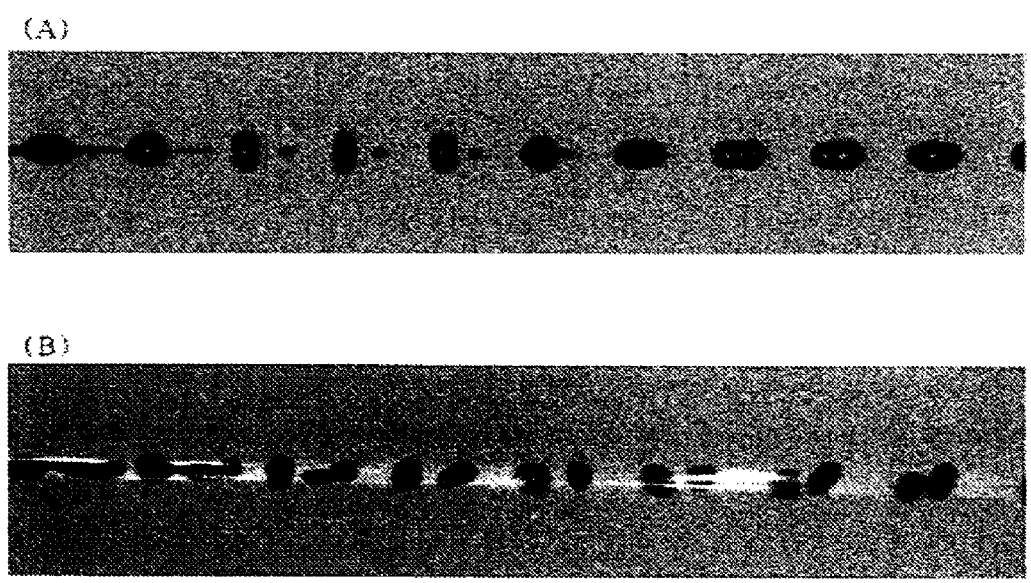
FIGS. 9A and 9B is a photograph showing a typical example of the shape of droplets ejected from the microchip 1 (A) according to the embodiment of the present disclosure and a typical example of the shape of droplets ejected from a microchip in the related art shown in FIG. 10 (B)
Figure 10:
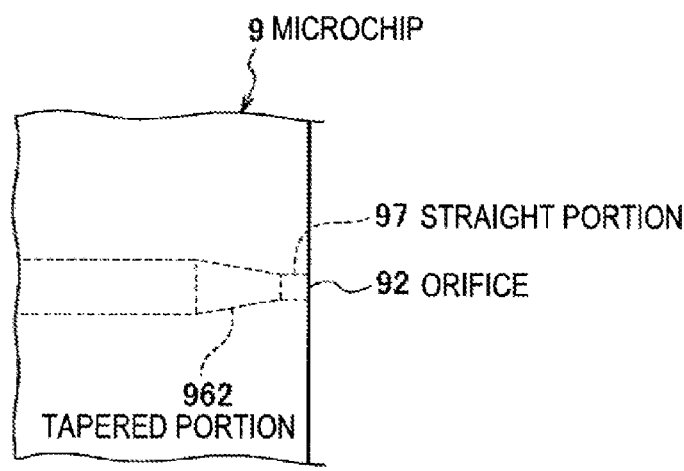
FIGS. 10A through 10C is schematic diagrams illustrating a configuration of an orifice of the microchip in the related art.
Figure 10:
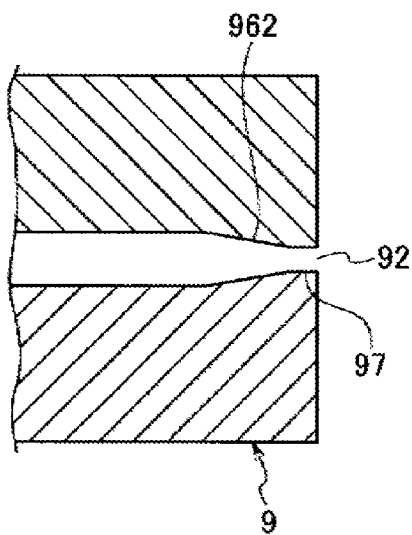
Figure 10:
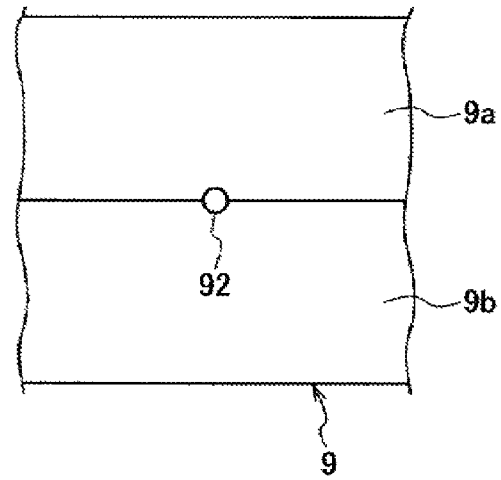

For comparison, an orifice configuration of a microchip 9 in the related art will be described with reference to FIG. 10. The microchip 9 in the related art does not include any mechanism that may be corresponded to the cutout portion 121 of the present embodiment. For reference, FIG. 9 shows the shape of droplets ejected from the microchip 1 according to the embodiment of the present disclosure and the shape of droplets ejected from the microchip 9 in the related art. FIG. 9A shows a typical example of shapes of droplets ejected from the microchip 1 and FIG. 9B shows a typical example of shapes of droplets ejected from the microchip 9.

The microchip according to the embodiment of the present disclosure includes the cutout portion allowing the shape irregularity or deformation of the orifice and flow channel caused due to injection molding and thermocompression bonding in the substrate layer to be prevented. According to the microchip of the embodiment, the droplets of regular size and shape can be stably ejected from the uniform shaped orifice in a steady ejecting path.

In the microchip according to the embodiment of the present disclosure, the orifice and flow channel having a uniform shape can be formed by injection molding and thermocompression bonding processes using thermoplastic resin without performing the polishing process on expensive quartz and ceramic such as alumina and zirconia, thereby saving the cost and increasing the productivity. Furthermore, According to the microchip of the embodiment of the present disclosure, the orifice is not provided at the distal end of the microchip, and thus breakage of the orifice due to an accidental contact probably occurred during the manufacturing process is unlikely to happen, thereby increasing the productivity.

3. Operation of Particle Analyzing Apparatus

Figure 8:
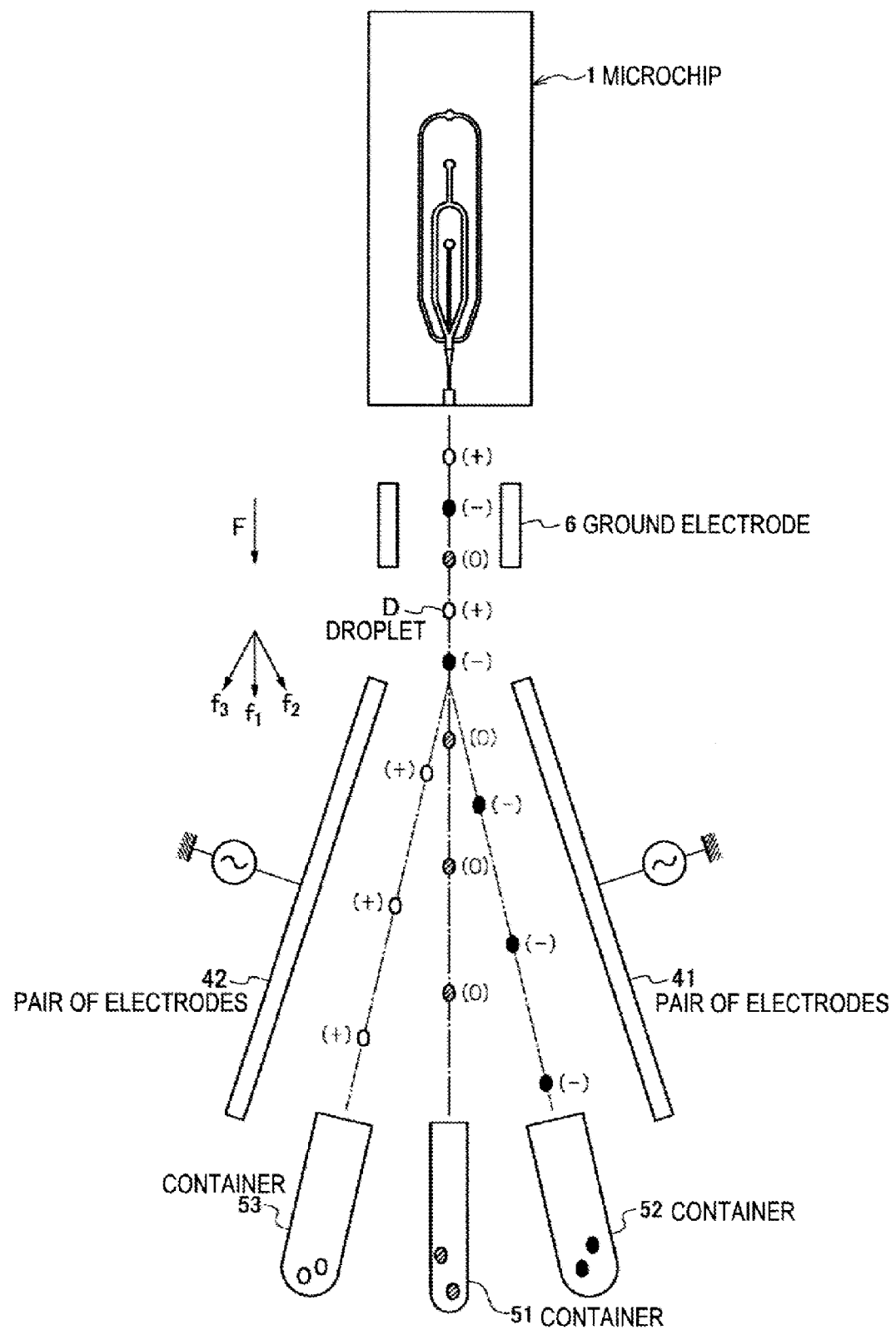
FIG. 8 is a schematic diagram illustrating a particle sorting operation of the particle analyzing apparatus A according to an embodiment of the present disclosure.

An operation of the particle analyzing apparatus A will be described with reference to FIG. 8.

The joined sample and sheath fluids, which are passed through the light irradiation area of the sample flow channel 11, are ejected from the orifice 12 to the outside of the microchip 1. In the light irradiation area, the optical detection unit detects the optical characteristics of the particles and simultaneously detects the fluid flowing speed (flow rate) of the particles and the interval between the particles. The optical characteristics, flow rate, interval and the like of the particles detected by the optical detection unit are converted into respective electrical signals. The electrical signals are outputted to a controller (not shown) configured to control the entire apparatus. The controller controls a vibration frequency of the vibrating device 2 (see FIG. 4) based on the electrical signals, and the controller vibrates the microchip 1 in such a way that the particle P is suspended in the droplet D one particle at a time.

In addition, the controller causes the polarity of electric charge applied to each of the sheath and sample fluids flowing through the sample flow channel 11 to be changed in synchronization with the vibration frequency of the vibrating device 2. Thus, individual droplets formed in the orifice 12 can be electrically charged by the controller and will carry a positive or negative charge.

The optical characteristics of the particle detected by the optical detection unit are converted into the electrical signal. The electrical signal is outputted to the controller. The controller determines which electric charge will be applied to the droplet based on the electrical signal, in accordance with the optical characteristics of the particle contained in each of the droplets. More specifically, when the droplets are electrically charged by the controller, the droplet containing the particle to be sorted with desired characteristics may be positively charged, and the droplet which is not containing the particle to be sorted may be negatively charged.

In this case, in order to stabilize the electrically charged state of the droplet D, in the particle analyzing apparatus A, the ground electrodes 6, 6 are disposed in the vicinity of the orifice 12 along the flow direction of the droplet being ejected to the outside of the microchip. The ground electrodes 6, 6 are arranged to be faced each other and to allow the droplets to be flowed between the electrodes. The ground electrodes 6, 6 are disposed between the orifice 12 and a pair of electrodes 41, 42. The pair of electrodes 41, 42 controls the flow direction of the droplets.

The flow direction of the charged droplet D ejected from the orifice 12 is controlled by electrostatic force acting between the electrodes 41 and 42. In this case, the stable application of the electric charge to the droplet is necessary in order to accurately control the flow direction of the droplet. At this time, a very high voltage is applied between the pair of electrodes 41 and 42, and thus the electrically charged state of the droplet D is likely to become unstable. To overcome this, in the particle analyzing apparatus A, the ground electrodes 6, 6 are disposed between the orifice 12 and the pair of electrode 41, 42, thereby eliminating the influence of the high potential applied between the pair of electrode 41, 42.

Controlling the flow direction of the droplet D ejected from the orifice 12, for example, is carried out as follows. In the previous described case where the droplet containing the particle to be sorted may be positively charged and the droplet not containing the particle to be sorted may be negatively charged, when the electrode 41 is positively charged and the electrode 42 is negatively charged, the droplet containing the particle to be sorted can be deflected and sorted into the container 53. More specifically, when the droplet containing the particle to be sorted is positively charged, the flow of the positively charged droplet is deflected into a direction indicated by an arrow f3 by the electrostatic repulsive force acting between the electrode 41 and the droplet and by the electrostatic attractive force acting between the electrode 42 and the droplet. The deflected droplet then moves toward the container 53. On the other hand, when the droplet not containing the particle to be sorted is negatively charged, the flow of the negatively charged droplet is deflected into a direction indicated by an arrow f2, and then the droplet moves toward the container 52.

When the droplet containing the particle to be sorted remains uncharged, the droplet not containing the particle to be sorted is positively or negatively charged, and each of the electrodes 41, 42 are either positively or negatively charged, then the droplet containing the particle to be sorted can be deflected and sorted into the container 51. The application of the electric charge to the droplet D and the control of the droplet flowing direction by the electrodes 41, 42 can be performed using various kinds of combinations in a similar way to the flow cytometry in the related art. It is noted that two or more containers for receiving the droplets D may be provided and the number of containers is not limited to three. In addition, the container may be configured to work as an ejection channel for ejecting the collected droplets without accommodating the collected droplets. When the particle not to be sorted is collected, the particle may be discarded.

As described above, according to the microchip 1, the droplet D of regular size and shape can be stably ejected from the uniform shaped orifice 12 in a steady ejecting path. Thus, according to the microchip 1, the flow direction of the droplet D can be precisely controlled and the particles with desired characteristics can be correctly sorted.

The description has been given with respect to the case where positive or negative electric charge is correspondingly applied to individual droplets depending on the characteristics of the particle contained in the droplet and then the droplet is sorted. Even when the optical detection unit is replaced with an electrical or magnetic detecting mechanism, controlling of the flow direction of the droplet based on electrical or magnetic characteristics allows sorting of the droplet, thus the particles with desired characteristics can be diverted and sorted into the individual containers.

Additionally, the present technology may also be configured as below.

(1) A microchip including:

a flow channel configured to convey a fluid therein;

an ejection portion including an opening directed toward an end face of a substrate layer, the ejection portion configured to eject the fluid flowing through the flow channel to outside, the substrate layer being laminated to each other; and a cutout portion formed between the opening of the ejection portion and the end face of the substrate layer, the cutout portion having a larger diameter than that of the opening.

(2) The microchip according to claim 1, further including:
a connection portion, configured to have a straight line shape, for connecting the flow channel to the ejection portion.

(3) The microchip according to claim 2, wherein
the substrate layer is formed by injection molding.

(4) The microchip according to claim 3, wherein
the substrate layer is laminated by thermocompression bonding.

(5) The microchip according to claim 4, wherein
the cutout portion has a width of 0.2 millimeters or more in corresponding with a distance between the opening and the end face.

(6) The microchip according to claim 5, wherein
the microchip is used in analyzing particles.

(7) A particle analyzing apparatus having the microchip as recited in claim 6 mounted thereon.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

A Particle analyzing apparatus
$A_1$ Main body
$A_2$ Cover
$A_3$ Sorting cover
D droplet
P Particle(s)
1 Microchip
1a, 1b Substrate layer
11 Sample flow channel
12 Orifice
121 Cutout portion
13 Sample fluid inlet
14 Sheath fluid inlet
15 Suction channel
151 Suction outlet
152 Communicating port
161, 162 Tapered portion
17 Straight portion
2 Vibrating device
3 Optical detection unit
4, 41, 42 Paired Electrode
51, 52, 53 Collection vessel (container)
6 Ground electrode

The invention claimed is:

1. A microchip comprising:
a flow channel configured to convey a fluid therein;
an ejection portion including an opening directed toward an end face of a substrate layer, the ejection portion configured to eject the fluid flowing through the flow channel to outside, and
a cutout portion formed between the opening of the ejection portion and the end face of the substrate layer, the cutout portion having a larger diameter than that of the opening of the ejection portion,
wherein at least a portion of the cutout portion is provided at the end face of the substrate layer.

2. The microchip according to claim 1, further comprising:
a connection portion, having a straight line shape for connecting the flow channel to the ejection portion.

3. The microchip according to claim 2, wherein
the substrate layer is formed by injection molding.

4. The microchip according to claim 3, wherein
the substrate layer is laminated by thermocompression bonding.

5. The microchip according to claim 4, wherein
the cutout portion has a width of 0.2 millimeters or more in corresponding with a distance between the opening of the ejection portion and the end face of the substrate layer.

6. The microchip according to claim 5, wherein
the microchip is configured to be used in a particle analyzing apparatus.

7. The microchip according to claim 1, wherein an opening of the cutout portion includes an octagonal prism shape.

8. The microchip according to claim 1, further comprising a suction channel, wherein the suction channel is connected with the flow channel via a communicating port.

9. The microchip according to claim 1, further comprising a tapered portion, wherein the tapered portion is provided between the flow channel and the communicating port.

10. A particle analyzing apparatus comprising:
a microchip, an optical detector and a pair of electrodes,
wherein the microchip includes
a flow channel configured to convey a fluid therein;
an ejection portion including an opening directed toward an end face of a substrate layer, the ejection portion configured to eject the fluid flowing through the flow channel to outside, and
a cutout portion formed between the opening of the ejection portion and the end face of the substrate layer, the cutout portion having a larger diameter than that of the opening of the ejection portion,
wherein at least a portion of the cutout portion is provided at the end face of the substrate layer.

11. The particle analyzing apparatus according to claim 10, wherein an opening of the cutout portion includes an octagonal prism shape.

12. The particle analyzing apparatus according to claim 10, wherein the optical detector includes a laser light source, an irradiation system and a detection system.

13. The particle analyzing apparatus according to claim 10, further comprising a vibrating device, wherein the vibrating device is configured to vibrate the microchip.

14. The particle analyzing apparatus according to claim 10, further comprising a ground electrode, wherein the ground electrode is provided between the cutout portion and the pair of electrodes.

* * * * *